US012582349B2

(12) United States Patent
Matsumoto

(10) Patent No.: US 12,582,349 B2
(45) Date of Patent: Mar. 24, 2026

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Tsuyoshi Matsumoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 432 days.

(21) Appl. No.: 18/311,655

(22) Filed: May 3, 2023

(65) Prior Publication Data

US 2023/0270375 A1     Aug. 31, 2023

Related U.S. Application Data

(63) Continuation of application No. PCT/JP2021/036584, filed on Oct. 4, 2021.

(30) Foreign Application Priority Data

Nov. 27, 2020    (JP) ................................. 2020-196556

(51) Int. Cl.
*A61B 5/00*          (2006.01)

(52) U.S. Cl.
CPC .... *A61B 5/4542* (2013.01); *A61B 2562/0219* (2013.01)

(58) Field of Classification Search
CPC ..... A61B 5/4542; A61B 5/1114; A61B 5/228; A61B 5/389; A61B 5/7267; A61B 5/4205;

(Continued)

(56) References Cited

U.S. PATENT DOCUMENTS 7,914,468 B2 *   3/2011   Shalon ................. A61B 5/0006
                                                             600/595
2014/0236262 A1   8/2014   You et al.
2015/0313572 A1 *  11/2015   Gerbaulet .............. A61C 19/04
                                                             433/29

FOREIGN PATENT DOCUMENTS

JP        2012-147757 A      8/2012
JP        2012-217525 A     11/2012
                  (Continued)

OTHER PUBLICATIONS

Van Den Engel-Hoek, L., Lagarde, M., & Van Alfen, N. (2017). Ultrasound of oral and masticatory muscles: Why every neuromuscular swallow team should have an ultrasound machine. Clinical Anatomy, 30(2), 183-193. (Year: 2017).*

(Continued)

*Primary Examiner* — Eric F Winakur
*Assistant Examiner* — Hy Khanh Doan
(74) *Attorney, Agent, or Firm* — Studebaker Brackett PLLC

(57) ABSTRACT

Provided are an ultrasound diagnostic apparatus and a control method for an ultrasound diagnostic apparatus capable of accurately evaluating dysphagia. The ultrasound diagnostic apparatus includes: an ultrasound probe; an image formation unit that acquires an ultrasound image of a pharyngeal part of a subject in accordance with an image formation condition by transmitting and receiving an ultrasound beam using the ultrasound probe; a chewing information acquisition unit that acquires chewing information during chewing of the subject; an image formation condition adjustment unit that adjusts the image formation condition on the basis of the chewing information acquired by the chewing information acquisition unit; and a swallowing evaluation unit that evaluates swallowing of the subject, on the basis of the ultrasound image acquired by the image (Continued)

formation unit in accordance with the image formation condition adjusted by the image formation condition adjustment unit.

20 Claims, 6 Drawing Sheets

(58) Field of Classification Search
  CPC ....... A61B 8/08; A61B 8/5223; A61B 8/5207;
      A61B 2562/0219
  See application file for complete search history.

(56) References Cited

FOREIGN PATENT DOCUMENTS

| | | | |
|---|---|---|---|
| JP | 2014-529413 A | 11/2014 | |
| JP | 2019-104733 A | 6/2019 | |
| JP | 2020-089613 A | 6/2020 | |
| WO | WO-2018207935 A1 * | 11/2018 | ........... A61B 8/4477 |

OTHER PUBLICATIONS

International Search Report issued in PCT/JP2021/036584; mailed Dec. 14, 2021.
International Preliminary Report On Patentability (Chapter I) and Written Opinion of the International Searching Authority issued in PCT/JP2021/036584; issued May 30, 2023.

* cited by examiner

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

This application is a Continuation of PCT International Application No. PCT/JP2021/036584 filed on Oct. 4, 2021, which claims priority under 35 U.S.C. § 119(a) to Japanese Patent Application No. 2020-196556 filed on Nov. 27, 2020. The above applications are hereby expressly incorporated by reference, in their entirety, into the present application.

BACKGROUND OF THE INVENTION

1. Field of the Invention

The present invention relates to an ultrasound diagnostic apparatus that acquires an ultrasound image of a pharyngeal part of a subject to evaluate swallowing, and a control method for the ultrasound diagnostic apparatus.

2. Description of the Related Art

In recent years, as disclosed in JP2012-147757A, jelly foods for patients with deteriorated swallowing function have been distributed on the market. The shape, hardness, and the like of the jelly food are adjusted such that it is easy to swallow. However, in a case of a patient with dysphagia, the jelly food may sometimes remain in the vallecula, pyriform sinuses, or the like of the pharyngeal part. Therefore, the dysphagia is evaluated by bringing an ultrasound probe into contact with the pharyngeal part of a subject who has ingested the jelly food and capturing an ultrasound image of the pharyngeal part.

Here, the ultrasound image is generated by transmitting an ultrasound beam from the ultrasound probe toward the subject, receiving an ultrasound echo reflected in the body of the subject through the ultrasound probe, and electrically processing a reception signal.

Meanwhile, jelly used in jelly foods generally has a property of poorly reflecting the ultrasound beam and appearing difficult to visualize in the ultrasound image.

In addition, JP2019-104733A discloses a viscous air bubble liquid that can be used as a contrast agent for confirming a swallowing function in a field such as an ultrasound echo examination from the fact that air bubbles are a good reflection source of ultrasound waves.

In that respect, it has been found that generating a jelly food in which air bubbles that are likely to reflect ultrasound waves are mixed in the jelly improves the visibility of the jelly food in the ultrasound image and makes it easier to determine whether or not the jelly food remains in the pharyngeal part of the subject.

SUMMARY OF THE INVENTION

However, in a case in which a jelly food containing air bubbles is ingested, in response to chewing, the air bubbles are destroyed and the viscosity of the jelly decreases, which makes it easier to flow. Therefore, it becomes difficult to capture the jelly food that instantly remains in the pharyngeal part from the ultrasound image.

Furthermore, since subjects have individual differences in the number of chewing movements, strength, or the like of chewing and, as a result, the optimal timing for capturing the ultrasound image and the optimal image quality settings differ, there is a concern that the evaluation accuracy of dysphagia may decrease depending on individual differences in the subjects and the proficiency of an examiner.

The present invention has been made in order to solve such a conventional problem, and an object of the present invention is to provide an ultrasound diagnostic apparatus and a control method for an ultrasound diagnostic apparatus capable of accurately evaluating dysphagia.

In order to achieve the above object, according to the present invention, there is provided an ultrasound diagnostic apparatus comprising:

an ultrasound probe;

an image formation unit that acquires an ultrasound image of a pharyngeal part of a subject in accordance with an image formation condition by transmitting and receiving an ultrasound beam using the ultrasound probe;

a chewing information acquisition unit that acquires chewing information during chewing of the subject;

an image formation condition adjustment unit that adjusts the image formation condition on the basis of the chewing information acquired by the chewing information acquisition unit; and a swallowing evaluation unit that evaluates swallowing of the subject, on the basis of the ultrasound image acquired by the image formation unit in accordance with the image formation condition adjusted by the image formation condition adjustment unit.

It is preferable that the image formation unit acquires the ultrasound image of the pharyngeal part of the subject in a case in which a jelly food containing air bubbles is swallowed, in accordance with the image formation condition adjusted by the image formation condition adjustment unit.

The chewing information acquisition unit may acquire at least one of the number of chewing movements, a strength of chewing, a habit of chewing, or an area of chewing as the chewing information.

It is preferable that the image formation condition adjustment unit adjusts the image formation condition to increase brightness, contrast, and resolution as the number of chewing movements, the strength of chewing, or the area of chewing acquired as the chewing information by the chewing information acquisition unit increases.

Further, it is preferable that the image formation condition adjustment unit adjusts the image formation condition to increase a frame rate as the number of chewing movements, the strength of chewing, or the area of chewing acquired as the chewing information by the chewing information acquisition unit increases.

The chewing information acquisition unit may include a motion sensor that is attached to the subject and that detects a motion of at least one of a mouth, a jaw, or the pharyngeal part of the subject, and an analysis unit that acquires the chewing information by analyzing the motion detected by the motion sensor.

As the motion sensor, at least one of a myoelectric sensor, an acceleration sensor, or a vibration sensor may be used.

The chewing information acquisition unit may include a microphone that acquires a chewing sound, and an analysis unit that acquires the chewing information by analyzing the chewing sound acquired by the microphone.

Further, the chewing information acquisition unit may include an optical camera that acquires an optical image of a region including at least one of a mouth, a jaw, or the pharyngeal part of the subject, and an analysis unit that acquires the chewing information by analyzing the optical image acquired by the optical camera.

In this case, the analysis unit may acquire the chewing information by analyzing a video image acquired by the optical camera.

The image formation unit may have an initial parameter of the image formation condition set for each subject.

It is preferable that the image formation condition adjustment unit uses machine learning to adjust the image formation condition to an optimized condition on the basis of the chewing information.

According to the present invention, there is provided a control method for an ultrasound diagnostic apparatus, comprising:

acquiring chewing information during chewing of a subject;

adjusting an image formation condition on the basis of the acquired chewing information;

acquiring an ultrasound image of a pharyngeal part of the subject in accordance with the adjusted image formation condition by transmitting and receiving an ultrasound beam using an ultrasound probe; and evaluating swallowing of the subject on the basis of the acquired ultrasound image.

According to the present invention, the chewing information during chewing of the subject is acquired, the image formation condition is adjusted on the basis of the acquired chewing information, and swallowing of the subject is evaluated on the basis of the ultrasound image acquired in accordance with the adjusted image formation condition, so that dysphagia can be accurately evaluated.

DESCRIPTION OF THE PREFERRED EMBODIMENTS

Hereinafter, embodiments of the present invention will be described with reference to the accompanying drawings.

The following description of configuration requirements is made on the basis of a representative embodiment of the present invention, but the present invention is not limited to such an embodiment.

In the present specification, a numerical range represented by "to" means a range including numerical values before and after "to" as a lower limit value and an upper limit value.

In the present specification, "same" and "equal" include an error range generally allowed in the technical field.

Embodiment 1

Figure 1:
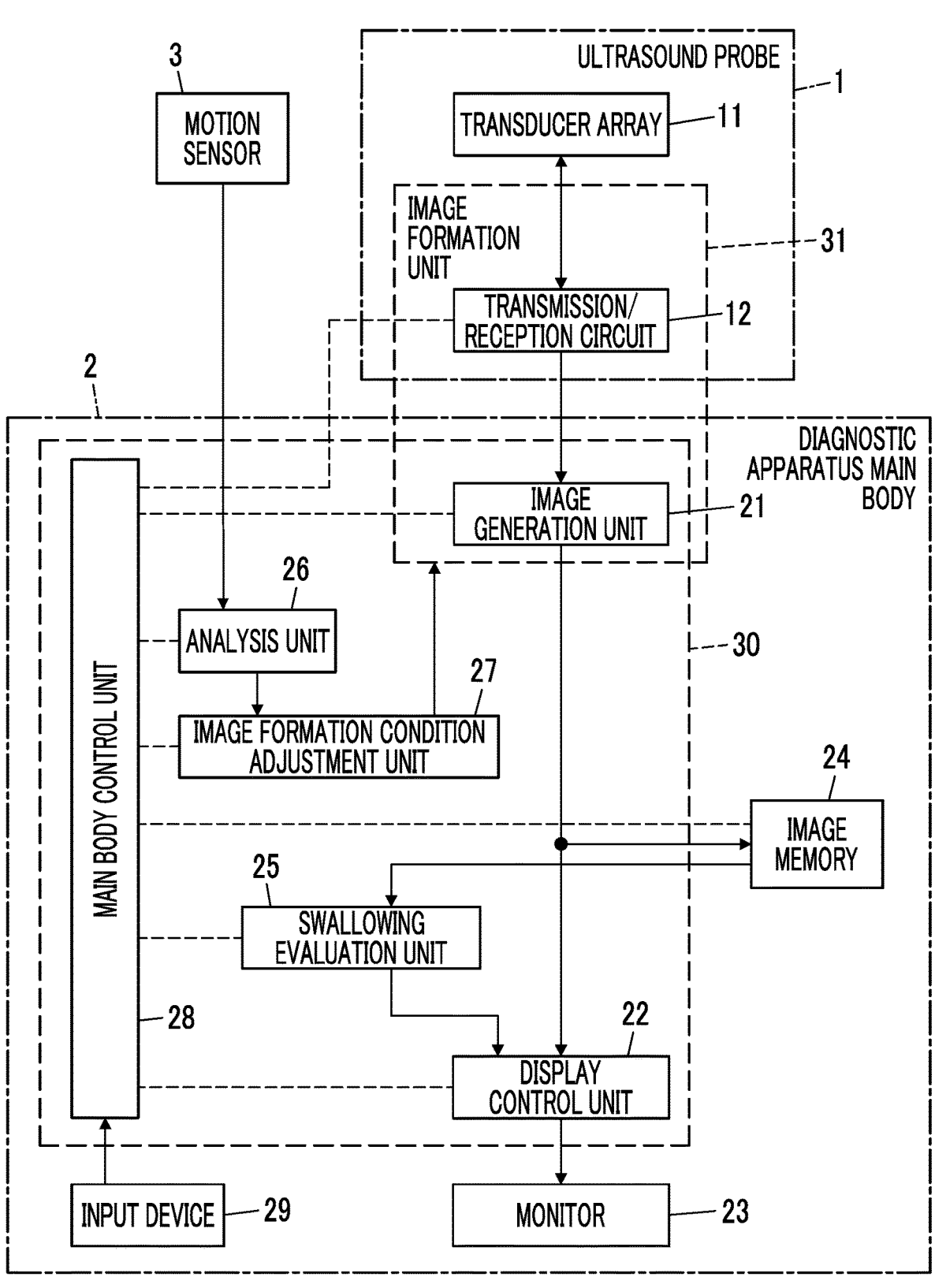
FIG. 1 is a block diagram showing a configuration of an ultrasound diagnostic apparatus according to Embodiment 1 of the present invention.

FIG. 1 shows a configuration of an ultrasound diagnostic apparatus according to Embodiment 1 of the present invention. The ultrasound diagnostic apparatus comprises an ultrasound probe 1, a diagnostic apparatus main body 2, and a motion sensor 3. Each of the ultrasound probe 1 and the motion sensor 3 is connected to the diagnostic apparatus main body 2.

The ultrasound probe 1 includes a transducer array 11, and a transmission/reception circuit 12 is connected to the transducer array 11.

The diagnostic apparatus main body 2 includes an image generation unit 21 connected to the transmission/reception circuit 12 of the ultrasound probe 1, and a display control unit 22 and a monitor 23 are sequentially connected to the image generation unit 21. In addition, an image memory 24 is connected to the image generation unit 21, and a swallowing evaluation unit 25 is connected to the image memory 24. The swallowing evaluation unit 25 is connected to the display control unit 22.

In addition, the diagnostic apparatus main body 2 includes an analysis unit 26, and an image formation condition adjustment unit 27 is connected to the analysis unit 26.

Further, the diagnostic apparatus main body 2 includes a main body control unit 28, and the image generation unit 21, the display control unit 22, the image memory 24, the swallowing evaluation unit 25, the analysis unit 26, and the image formation condition adjustment unit 27, and the transmission/reception circuit 12 of the ultrasound probe 1 are connected to the main body control unit 28.

In addition, an input device 29 is connected to the main body control unit 28.

A processor 30 is composed of the image generation unit 21, the display control unit 22, the swallowing evaluation unit 25, the analysis unit 26, the image formation condition adjustment unit 27, and the main body control unit 28.

An image formation unit 31 is formed of the transmission/reception circuit 12 of the ultrasound probe 1 and the image generation unit 21 of the diagnostic apparatus main body 2, and the image formation condition adjustment unit 27 of the diagnostic apparatus main body 2 is connected to the image formation unit 31.

The transducer array 11 of the ultrasound probe 1 includes a plurality of ultrasound transducers one-dimensionally or two-dimensionally arranged. Each of these transducers transmits an ultrasound wave in accordance with a drive signal supplied from the transmission/reception circuit 12 and outputs an analog reception signal by receiving a reflected wave from the subject. For example, each transducer is composed of a piezoelectric body containing piezoelectric ceramic represented by Lead Zirconate Titanate (PZT), a polymer piezoelectric element represented by Poly Vinylidene Di Fluoride (PVDF), piezoelectric single crystal represented by Lead Magnesium Niobate-Lead Titanate (PMN-PT), or the like, and electrodes formed at both ends of the piezoelectric body.

Figure 2:
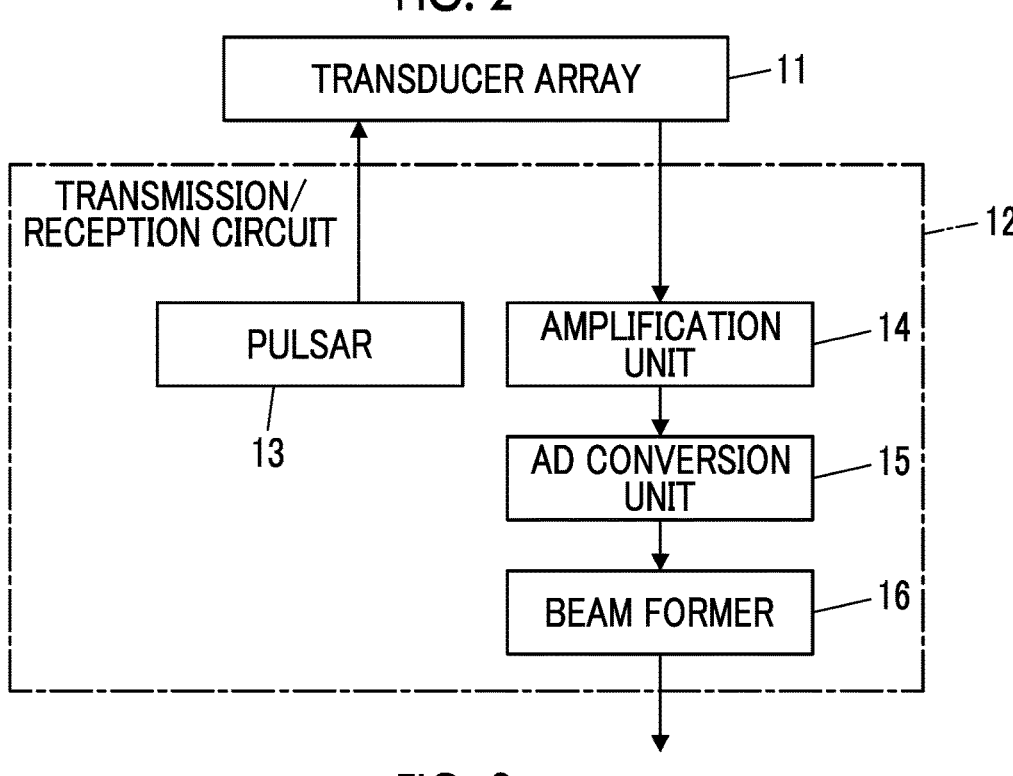
FIG. 2 is a block diagram showing an internal configuration of a transmission/reception circuit in Embodiment 1.

Under the control of the main body control unit 28 of the diagnostic apparatus main body 2, the transmission/reception circuit 12 transmits ultrasound waves from the transducer array 11 and generates a sound ray signal on the basis of the reception signal acquired by the transducer array 11. As shown in FIG. 2, the transmission/reception circuit 12 includes a pulsar 13 connected to the transducer array 11, an amplification unit 14, an analog-to-digital (AD) conversion unit 15, and a beam former 16 that are sequentially connected in series to the transducer array 11.

The pulsar 13 includes, for example, a plurality of pulse generators, and supplies respective drive signals to the plurality of transducers by adjusting amounts of delay such that ultrasound waves transmitted from the plurality of transducers of the transducer array 11 form an ultrasound beam, on the basis of a transmission delay pattern selected according to a control signal from the main body control unit 28. In this way, in a case in which a pulsed or continuous-wave voltage is applied to the electrodes of the transducer of the transducer array 11, the piezoelectric body expands and contracts, and a pulsed or continuous-wave ultrasound wave is generated from each of the transducers, whereby the ultrasound beam is formed from a combined wave of these ultrasound waves.

The transmitted ultrasound beam is reflected in, for example, a site in the subject and a target such as a food ingested in the subject, and the ultrasound echo propagates toward the transducer array 11 of the ultrasound probe 1. The ultrasound echo propagating toward the transducer array 11 in this way is received by each of the transducers constituting the transducer array 11. At this time, each of the transducers constituting the transducer array 11 expands and contracts by receiving the propagating ultrasound echo, generates a reception signal, which is an electrical signal, and outputs the reception signal to the amplification unit 14.

The amplification unit 14 amplifies the signal input from each of the transducers constituting the transducer array 11 and transmits the amplified signal to the AD conversion unit 15. The AD conversion unit 15 converts the signal transmitted from the amplification unit 14 into digital reception data and transmits the reception data to the beam former 16. The beam former 16 performs so-called reception focus processing by giving and adding delay with respect to each reception data converted by the AD conversion unit 15, in accordance with a sound speed or a sound speed distribution set on the basis of a reception delay pattern selected according to a control signal from the main body control unit 28. By this reception focus processing, each reception data converted by the AD conversion unit 15 is phase-added, and a sound ray signal in which the focus of the ultrasound echo is narrowed down is acquired.

Figure 3:
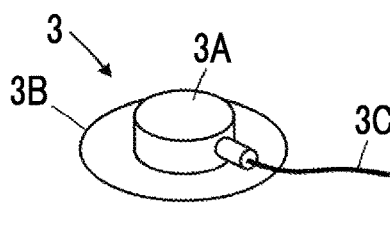
FIG. 3 is a perspective view showing a myoelectric sensor used in Embodiment 1.

The motion sensor 3 is attached to the subject and detects the motion of at least one of the mouth, the jaw, or the pharyngeal part of the subject. As the motion sensor 3, for example, a myoelectric sensor as shown in FIG. 3 can be used. The myoelectric sensor includes a sensor main body 3A and an adhesive seal 3B attached to the sensor main body 3A, is attached to the body surface of the subject using the adhesive seal 3B, and is connected to the analysis unit 26 of the diagnostic apparatus main body 2 via a cable 3C pulled out from the sensor main body 3A.

The sensor main body 3A includes an electrode (not shown), and detects a myoelectric potential generated in a case in which muscle cells of the subject perform contraction activities, via the electrode. It is possible to grasp the motion of the muscle on the basis of the myoelectric potential detected by the sensor main body 3A.

By bonding and attaching such a motion sensor 3 to a temple, a jawline, or the like of the subject, it is possible to detect motions of the mouth, the jaw, the pharyngeal part, and the like of the subject through the motions of muscles.

In order to more accurately detect the motions of the mouth, the jaw, the pharyngeal part, and the like of the subject, it is preferable that a plurality of myoelectric sensors attached to the left and right sides or the like of the face of the subject are used as the motion sensor 3 to grasp the motions of a plurality of muscles.

Figure 4:
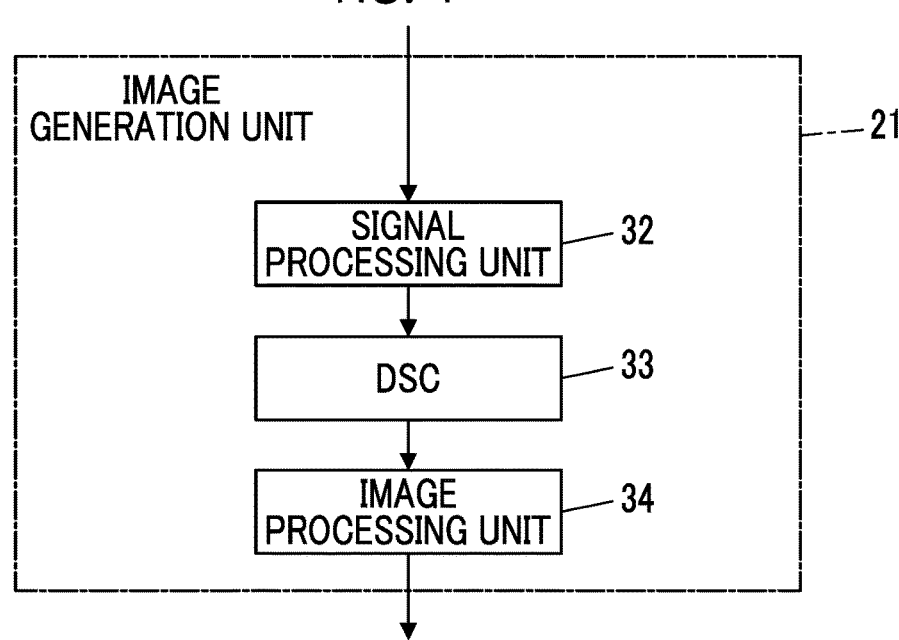
FIG. 4 is a block diagram showing an internal configuration of an image generation unit in Embodiment 1.

As shown in FIG. 4, the image generation unit 21 of the diagnostic apparatus main body 2 has a configuration in which a signal processing unit 32, a digital scan converter (DSC) 33, and an image processing unit 34 are sequentially connected in series.

The signal processing unit 32 corrects attenuation caused by a distance according to the depth of reflection position of the ultrasound wave and then performs envelope detection processing, on the sound ray signal sent from the beam former 16 of the transmission/reception circuit 12 of the ultrasound probe 1, thereby generating an ultrasound image signal (B-mode image signal) which is tomographic image information regarding the tissue inside the subject.

The DSC 33 converts (raster-converts) the ultrasound image signal generated by the signal processing unit 32 into an image signal conforming to a scanning method of a normal television signal.

The image processing unit 34 performs various types of necessary image processing, such as gradation processing, on the ultrasound image signal input from the DSC 33, and then outputs a signal representing an ultrasound image to the display control unit 22 and the image memory 24. The signal representing an ultrasound image generated by the image generation unit 21 in this manner will be simply referred to as an ultrasound image.

Under the control of the main body control unit 28, the display control unit 22 performs predetermined processing on the ultrasound image sent from the image generation unit 21 and displays the ultrasound image on the monitor 23.

The monitor 23 displays the ultrasound image under the control of the display control unit 22, and examples thereof include a display device, such as a liquid crystal display (LCD) and an organic electroluminescence display (organic EL display).

The image memory 24 is a memory that stores a plurality of frames of ultrasound images. For example, the image memory 24 can hold a series of the plurality of frames of ultrasound images generated by the image generation unit 21 and obtained by capturing the pharyngeal part of the subject in response to the diagnosis related to the dysphagia of the subject.

As the image memory 24, recording media, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The swallowing evaluation unit 25 evaluates the swallowing of the subject by analyzing the ultrasound image stored in the image memory 24. The swallowing evaluation unit 25 analyzes the ultrasound image obtained by capturing the pharyngeal part of the subject to detect, for example, the presence or absence of a swallowing residue, such as food jelly, in the vallecula, the pyriform sinus, and the like of the pharyngeal part, the size of the swallowing residue, and the like.

Although the present invention is not particularly limited, the swallowing evaluation unit 25 can detect the presence or absence of the swallowing residue, the size thereof, and the like in the ultrasound image by using at least one of a determination model that has been trained using a machine learning technique such as deep learning, template matching, or an image analysis technique using a feature amount, such as adaptive boosting (Adaboost), support vector machine (SVM), or scale-invariant feature transform (SIFT).

The determination model is a trained model that has learned the relationship between a training ultrasound image, in which the pharyngeal part is captured, and the presence or absence of the swallowing residue and the size thereof in the training ultrasound image by using the training ultrasound image and the presence or absence of the swallowing residue and the size thereof in the training ultrasound image as training data, for a plurality of pieces of the training data.

The swallowing evaluation unit 25 evaluates the presence or absence of dysphagia of the subject and the degree of the dysphagia on the basis of the presence or absence of the swallowing residue in the ultrasound image, the size thereof, and the like, and sends the evaluation result to the display control unit 22.

The analysis unit 26 constitutes a chewing information acquisition unit together with the motion sensor 3, and analyzes the motion of at least one of the mouth, the jaw, or the pharyngeal part of the subject detected by the motion sensor 3 to acquire chewing information regarding the chewing of the subject. The analysis unit 26 can acquire, for example, at least one of the number of chewing movements, the strength of chewing, the habit of chewing, or the area of chewing of the subject to which the motion sensor 3 is attached, as the chewing information.

For example, the analysis unit 26 can measure the number of chewing movements by grasping the chewing from the repeated pattern of the myoelectric potential change on the basis of the myoelectric potential of the muscle detected by the myoelectric sensor attached to the temple, the jawline, or the like of the subject, and by counting the number of the repeated patterns.

In addition, the analysis unit 26 can acquire the strength of chewing of the subject from the level of the intensity of the myoelectric potential detected by the myoelectric sensor. The level of the intensity of the myoelectric potential may be ranked.

Further, the analysis unit 26 can acquire the habit of chewing, such as chewing only on either the left or right side of the oral cavity or having an imbalance in the strength of chewing between the left and right sides of the oral cavity, by analyzing the balance of chewing on the left and right sides in the oral cavity of the subject on the basis of the myoelectric potential detected by each of the plurality of myoelectric sensors attached to the left and right sides and the like of the face of the subject.

In addition, the analysis unit 26 can acquire the area of chewing of the subject by analyzing the amount of muscle used for chewing on the basis of the myoelectric potential detected by each of the plurality of myoelectric sensors attached to the subject.

The more the number of chewing movements of the subject is, the stronger the strength of chewing is, and the larger the area of chewing is, the more finely the ingested food is crushed in the oral cavity of the subject, making it easier to swallow. In addition, in a case of a subject having a habit of chewing only on either the left or right side of the oral cavity or a habit of having the imbalance in the strength of chewing or the area of chewing on the left or right side of the oral cavity, there is a probability that some parts of the ingested food that are difficult to crush and swallow may remain even in a case in which the number of chewing movements is large.

The image formation condition adjustment unit 27 adjusts an image formation condition in the image formation unit 31 formed by the transmission/reception circuit 12 of the ultrasound probe 1 and the image generation unit 21 of the diagnostic apparatus main body 2 to the optimal condition for the subject on the basis of the chewing information of the subject acquired by the analysis unit 26. Here, examples of the image formation condition can include parameters such as gain (brightness), contrast, resolution, and frame rates. In addition, whether or not multi-line processing such as harmonic imaging is employed can be included as one of the image formation conditions.

For example, in a case in which a jelly food containing air bubbles is ingested, the more the number of chewing movements is, the more the air bubbles are destroyed and the amount of ultrasound echo from the jelly food decreases. Therefore, the image formation condition adjustment unit 27 adjusts the image formation condition in the image formation unit 31 to increase the gain, the contrast, and the resolution, so that it is possible to acquire an ultrasound image having an image quality suitable for detecting the swallowing residue.

Similarly, the more the number of chewing movements is, the viscosity of the jelly decreases and the jelly food easily flows. Therefore, the image formation condition adjustment unit 27 adjusts the image formation condition in the image formation unit 31 to increase the frame rate, so that it possible to acquire an ultrasound image at a timing suitable for detecting the swallowing residue.

In addition, the stronger the strength of chewing is or the larger the area of chewing is, the more the air bubbles are destroyed and the jelly is crushed. Therefore, the image formation condition adjustment unit 27 adjusts the image formation condition in the image formation unit 31 to increase the gain, the contrast, and the resolution and to further increase the frame rate, so that it is possible to acquire an ultrasound image suitable for detecting the swallowing residue.

Further, in a case in which the chewing on the left and right sides in the oral cavity is uniform, the destruction of air bubbles and the crushing of the jelly are promoted as compared with a case of a habit of having the imbalance in the chewing on the left and right sides. Therefore, the image formation condition adjustment unit 27 adjusts the image formation condition in the image formation unit 31 to increase the gain, the contrast, and the resolution and to further increase the frame rate, so that it is possible to acquire an ultrasound image suitable for detecting the swallowing residue.

Although the present invention is not particularly limited, the image formation condition adjustment unit 27 can adjust the image formation condition in the image formation unit 31 to the optimal condition for the subject by using the determination model that has been trained using a machine learning technique such as deep learning.

The determination model is a trained model that has learned the relationship between the chewing information and the image formation condition by using the chewing information of a plurality of patients and the image formation conditions suitable for the plurality of patients as training data, for a plurality of pieces of training data.

The main body control unit 28 controls each unit of the diagnostic apparatus main body 2 on the basis of a control program or the like stored in advance.

Further, although not shown, a storage unit that stores a control program or the like of the diagnostic apparatus main body 2 is connected to the main body control unit 28. As the storage unit, for example, a flash memory, a RAM, an SD card, an SSD, or the like can be used.

The input device 29 is used for a user to perform an input operation and includes, for example, a keyboard, a mouse, a track ball, a touch sensor disposed by overlapping the monitor 23, and the like.

Although the processor 30 including the image generation unit 21, the display control unit 22, the swallowing evaluation unit 25, the analysis unit 26, the image formation condition adjustment unit 27, and the main body control unit 28 may be composed of a central processing unit (CPU) and a control program for causing the CPU to perform various types of processing, the processor 30 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the image generation unit 21, the display control unit 22, the swallowing evaluation unit 25, the analysis unit 26, the image formation condition adjustment unit 27, and the main body control unit 28 of the processor 30 can also be configured by being partially or wholly integrated into one CPU or the like.

Figure 5:
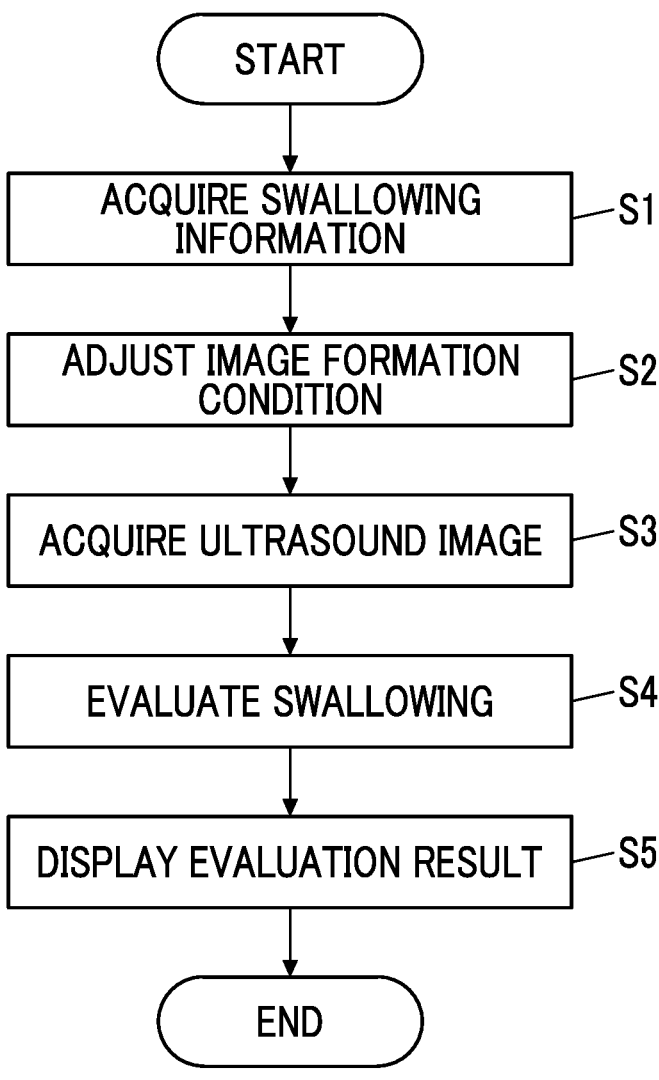
FIG. 5 is a flowchart showing an operation of the ultrasound diagnostic apparatus according to Embodiment 1.

Next, the operation of the ultrasound diagnostic apparatus according to Embodiment 1 of the present invention will be described with reference to the flowchart of FIG. 5.

It is assumed that a predetermined image formation condition is set in the image formation unit 31 formed by the transmission/reception circuit 12 of the ultrasound probe 1 and the image generation unit 21 of the diagnostic apparatus main body 2.

First, in step S1, in a state in which the motion sensor 3 is attached to the temple, the jawline, or the like of the subject and the ultrasound probe 1 is in contact with the pharyngeal part of the subject, the subject ingests the jelly food containing air bubbles, and the chewing information of the subject is acquired by the chewing information acquisition unit composed of the motion sensor 3 and the analysis unit 26. At this time, the motion of at least one of the mouth, the jaw, or the pharyngeal part of the subject who ingests the jelly food containing air bubbles is detected by the myoelectric sensor attached to the subject as the motion sensor 3, and the motion detected by the myoelectric sensor is analyzed by the analysis unit 26, whereby the chewing information consisting of at least one of the number of chewing movements, the strength of chewing, the habit of chewing, or the area of chewing of the subject is acquired.

Next, in step S2, on the basis of the chewing information acquired in step S1, the image formation condition in the image formation unit 31 is adjusted to the optimal condition for the subject by the image formation condition adjustment unit 27, and the adjusted new image formation condition is set to the transmission/reception circuit 12 of the ultrasound probe 1 and the image generation unit 21 of the diagnostic apparatus main body 2 constituting the image formation unit 31.

That is, the image formation condition including, for example, the gain (brightness), the contrast, the resolution, the frame rate, and the like is adjusted such that an ultrasound image having an image quality suitable for detecting the swallowing residue can be acquired, on the basis of the chewing information consisting of at least one of the number of chewing movements, the strength of chewing, the habit of chewing, or the area of chewing of the subject acquired in step S1.

In this manner, in a case in which the image formation condition set in the image formation unit 31 is adjusted to the optimal condition, the ultrasound image of the pharyngeal part of the subject during the swallowing of the jelly food containing air bubbles is acquired in accordance with the adjusted image formation condition, in step S3.

At this time, under the control of the main body control unit 28, transmission and reception of ultrasound waves are started from the plurality of transducers of the transducer array 11 in accordance with the drive signal from the pulsar 13 of the transmission/reception circuit 12, the ultrasound echo from the inside of the pharyngeal part of the subject is received by the plurality of transducers of the transducer array 11, and a reception signal which is an analog signal is output to the amplification unit 14 and amplified and is subjected to AD conversion by the AD conversion unit 15, so that reception data is acquired.

The reception focus processing is performed on this reception data by the beam former 16, the sound ray signal generated by this is sent to the image generation unit 21 of the diagnostic apparatus main body 2, and an ultrasound image representing tomographic image information regarding the inside of the pharyngeal part of the subject is generated by the image generation unit 21. At this time, the sound ray signal is subjected to the attenuation correction corresponding to the depth of the reflection position of the ultrasound wave and the envelope detection processing by the signal processing unit 32 of the image generation unit 21, is converted into the image signal conforming to the scanning method of the normal television signal by the DSC 33, and is subjected to various types of necessary image processing, such as gradation processing, by the image processing unit 34.

Since, in step S2, the image formation condition in the image formation unit 31 consisting of the transmission/reception circuit 12 and the image generation unit 21 is adjusted to the optimal condition on the basis of the chewing information of the subject, the ultrasound image generated by the image generation unit 21 is an image of an image quality and a timing suitable for detecting the swallowing residue of the subject, in step S3. The ultrasound image generated by the image generation unit 21 in this manner is sent to and stored in the image memory 24.

Then, in step S4, the ultrasound image acquired in step S3 and stored in the image memory 24 is analyzed by the swallowing evaluation unit 25, and the swallowing of the subject is evaluated. The swallowing evaluation unit 25 detects the presence or absence of the swallowing residue such as food jelly in the pyriform sinus of the pharyngeal part, the size of the swallowing residue, and the like from the ultrasound image, and evaluates whether or not the subject has dysphagia and the degree of dysphagia. Here, since the ultrasound image analyzed by the swallowing evaluation unit 25 is acquired in accordance with the image formation condition adjusted to the optimal condition for the subject, the swallowing residue can be detected with high accuracy, and the dysphagia can be accurately evaluated.

In the subsequent step S5, the evaluation result by the swallowing evaluation unit 25 is displayed on the monitor 23 via the display control unit 22 together with the ultrasound image used for detecting the swallowing residue. At this time, the waveform of the myoelectric potential detected by the myoelectric sensor may be displayed on the monitor 23 together with the ultrasound image and the evaluation result.

As described above, with the ultrasound diagnostic apparatus according to Embodiment 1, the chewing information acquisition unit composed of the motion sensor 3 and the analysis unit 26 acquires the chewing information during chewing of the subject, the image formation condition adjustment unit 27 adjusts the image formation condition in the image formation unit 31 to the optimal condition for the subject on the basis of the chewing information, the image formation unit 31 acquires the ultrasound image in accordance with the adjusted image formation condition, and the swallowing evaluation unit 25 evaluates the swallowing of the subject, so that dysphagia can be accurately evaluated.

In the ultrasound diagnostic apparatus, in a case in which a relatively high gain (brightness) and contrast, or a relatively high frame rate is set in advance as initial parameters of the image formation condition in the image formation unit 31 and the chewing information of the subject acquired by the analysis unit 26 indicates that the degree of chewing is relatively weak, the image formation condition adjustment unit 27 can also adjust the parameters such as the gain, the contrast, and the frame rate to be decreased. For example, since the degree of chewing is relatively weak, in a case in which the acquired number of chewing movements is less than a predetermined threshold value, in a case in which the strength of chewing is weaker than a predetermined threshold value, or in a case in which the area of chewing is smaller than a predetermined threshold value, it is preferable that the image formation condition adjustment unit 27 adjusts parameters such as the gain, the contrast, and the frame rate to be decreased.

By doing so, the visibility of the jelly food containing air bubbles in the ultrasound image is improved, and the power consumption of the ultrasound diagnostic apparatus is saved. Therefore, it is particularly effective for a portable or handheld type compact ultrasound diagnostic apparatus used at the bedside in home health nursing or the like.

The range of decreasing the parameters such as the gain, the contrast, and the frame rate may be determined according to the chewing information (the number of chewing movements, the strength of chewing, and the area of chewing) acquired by the analysis unit 26.

In addition, instead of decreasing parameters of the image formation condition such as the gain, the contrast, and the frame rate, the image formation condition adjustment unit 27 may adjust the image formation condition to employ multi-line processing such as harmonic imaging. Further, adjustment for decreasing parameters such as the gain, the contrast, and the frame rate can also be performed together with the employment of the multi-line processing such as harmonic imaging.

Since a subject with a relatively weak degree of chewing is likely to be a seriously ill patient, it is effective to employ the multi-line processing such as harmonic imaging in order to carefully detect the swallowing residue while achieving a high image quality.

In addition, a temporal change in the chewing information of the subject is acquired by the chewing information acquisition unit composed of the motion sensor 3 and the analysis unit 26, and the image formation condition adjustment unit 27 can also adjust the parameters of the image formation condition in real time in accordance with the acquired change in the chewing information. For example, the range of increasing or decreasing the parameters such as the gain and the contrast can be adjusted in conformity with an increase or decrease in the number of chewing movements acquired by the chewing information acquisition unit. As a result, it is possible to always acquire an ultrasound image suitable for detecting the swallowing residue even in a case in which the chewing information fluctuates.

In Embodiment 1 described above, the myoelectric sensor that detects the myoelectric potential is used as the motion sensor 3, but the present invention is not limited to this, and for example, an acceleration sensor may be used to detect the motion of at least one of the mouth, the jaw, or the pharyngeal part of the subject. The acceleration sensor is attached to the vicinity of the mouth, the jaw, the pharyngeal part, or the like of the subject, and the analysis unit 26 analyzes the acceleration waveform in the three-dimensional directions (X-axis, Y-axis, and Z-axis) acquired by the acceleration sensor, so that at least one of the number of chewing movements, the strength of chewing, the habit of chewing, or the area of chewing of the subject can be acquired as the chewing information.

Similarly, a vibration sensor may be used to detect the motion of at least one of the mouth, the jaw, or the pharyngeal part of the subject. The vibration sensor is attached to the vicinity of the mouth, the jaw, the pharyngeal part, and the like of the subject, and the analysis unit 26 analyzes the vibration waveform acquired by the vibration sensor, so that at least one of the number of chewing movements, the strength of chewing, the habit of chewing, or the area of chewing of the subject can be acquired as the chewing information.

Embodiment 2

Figure 6:
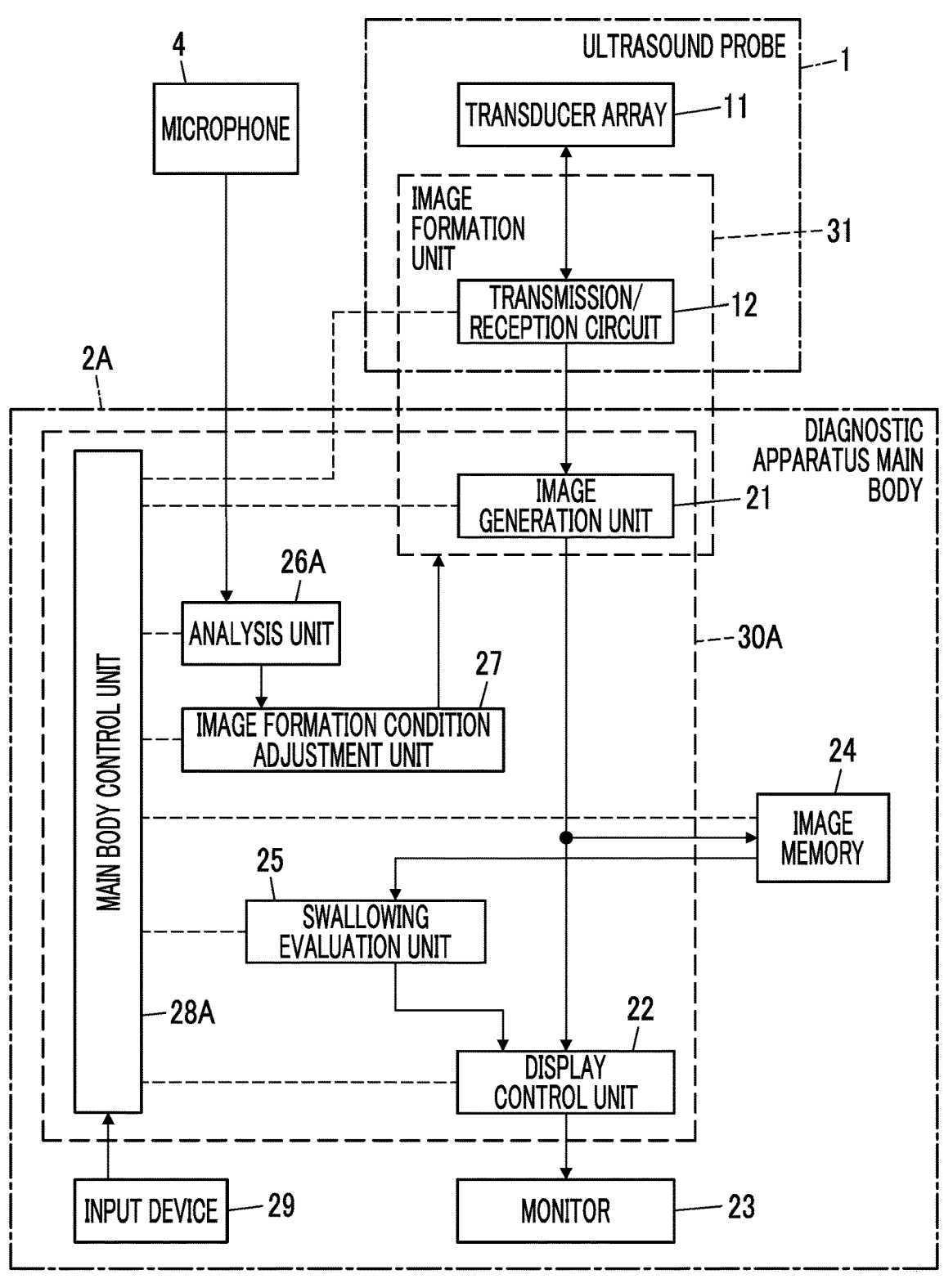
FIG. 6 is a block diagram showing a configuration of a diagnostic apparatus main body in Embodiment 2.

FIG. 6 shows a configuration of an ultrasound diagnostic apparatus according to Embodiment 2 of the present invention. The ultrasound diagnostic apparatus according to Embodiment 2 is an ultrasound diagnostic apparatus in which a microphone 4 is used instead of the motion sensor 3, a diagnostic apparatus main body 2A is used instead of the diagnostic apparatus main body 2, and the ultrasound probe 1 is connected to the diagnostic apparatus main body 2A in the ultrasound diagnostic apparatus of Embodiment 1 shown in FIG. 1. The diagnostic apparatus main body 2A uses an analysis unit 26A and a main body control unit 28A instead of the analysis unit 26 and the main body control unit 28 in the diagnostic apparatus main body 2 in Embodiment 1, and the other configurations are the same as those of the diagnostic apparatus main body 2 of Embodiment 1.

The ultrasound diagnostic apparatus according to Embodiment 2 acquires the chewing information of the subject by using sound.

The microphone 4 is disposed close to the pharyngeal part of the subject and is used for acquiring a swallowing sound of the subject during ingesting. The swallowing sound of the subject acquired by the microphone 4 is sent to the analysis unit 26A of the diagnostic apparatus main body 2A.

The microphone 4 may be incorporated in the ultrasound probe 1. In addition, the user may grip the microphone 4 independent of the ultrasound probe 1 and the diagnostic apparatus main body 2A and dispose the microphone 4 in the vicinity of the pharyngeal part of the subject, or can also attach the microphone 4 to a body surface portion of the pharyngeal part of the subject. Further, by holding the microphone 4 with a holder (not shown) that is hooked onto the neck or the like of the subject and is attached, the microphone 4 can be also disposed in the vicinity of the pharyngeal part of the subject.

The analysis unit 26A constitutes the chewing information acquisition unit together with the microphone 4, and acquires the chewing information regarding the chewing of the subject by analyzing the swallowing sound of the subject acquired by the microphone 4.

The analysis unit 26A can measure the number of chewing movements by grasping the chewing from the repeated pattern of the waveform of the swallowing sound and counting the number of the repeated patterns.

In addition, the analysis unit 26A can acquire the strength of chewing of the subject from the amplitude of the waveform of the swallowing sound.

Further, the analysis unit 26A can acquire the habit of chewing, such as chewing only on either the left or right side of the oral cavity or having an imbalance in the strength of chewing between the left and right sides of the oral cavity, by analyzing the balance of chewing on the left and right sides in the oral cavity of the subject on the basis of, for example, the waveform of the swallowing sound acquired by each of a plurality of the microphones 4 disposed on the left and right sides and the like of the face of the subject.

In the same manner, the analysis unit 26A can acquire the area of chewing of the subject by estimating the amount of muscle used for chewing on the basis of the waveform of the swallowing sound acquired by each of the plurality of microphones 4.

The image generation unit 21, the display control unit 22, the image memory 24, the swallowing evaluation unit 25, the analysis unit 26A, and the image formation condition adjustment unit 27, and the transmission/reception circuit 12 of the ultrasound probe 1 are connected to the main body control unit 28A, and the input device 29 is connected to the main body control unit 28A.

In addition, a processor 30A is composed of the image generation unit 21, the display control unit 22, the swallowing evaluation unit 25, the analysis unit 26A, the image formation condition adjustment unit 27, and the main body control unit 28A.

In the ultrasound diagnostic apparatus according to Embodiment 2, the chewing information of the subject is acquired by the chewing information acquisition unit composed of the microphone 4 and the analysis unit 26A, and the image formation condition in the image formation unit 31 is adjusted to the optimal condition for the subject by the image formation condition adjustment unit 27 on the basis of the acquired chewing information. Then, the ultrasound image of the pharyngeal part of the subject during the swallowing of the jelly food containing air bubbles is acquired in accordance with the adjusted image formation condition, and the swallowing of the subject is evaluated by the swallowing evaluation unit 25 through the analysis of the ultrasound image.

The evaluation result by the swallowing evaluation unit 25 is displayed on the monitor 23 via the display control unit 22 together with the ultrasound image used for detecting the swallowing residue. At this time, the waveform of the swallowing sound of the subject acquired by the microphone 4 can also be displayed on the monitor 23 together with the ultrasound image and the evaluation result.

Even in a case in which the chewing information acquisition unit is composed of the microphone 4 and the analysis unit 26A and the chewing information of the subject is acquired by using sound as in Embodiment 2, the ultrasound image can be acquired in accordance with the image formation condition adjusted to the optimal condition for the subject, and dysphagia can be accurately evaluated, as in Embodiment 1.

Embodiment 3

Figure 7:
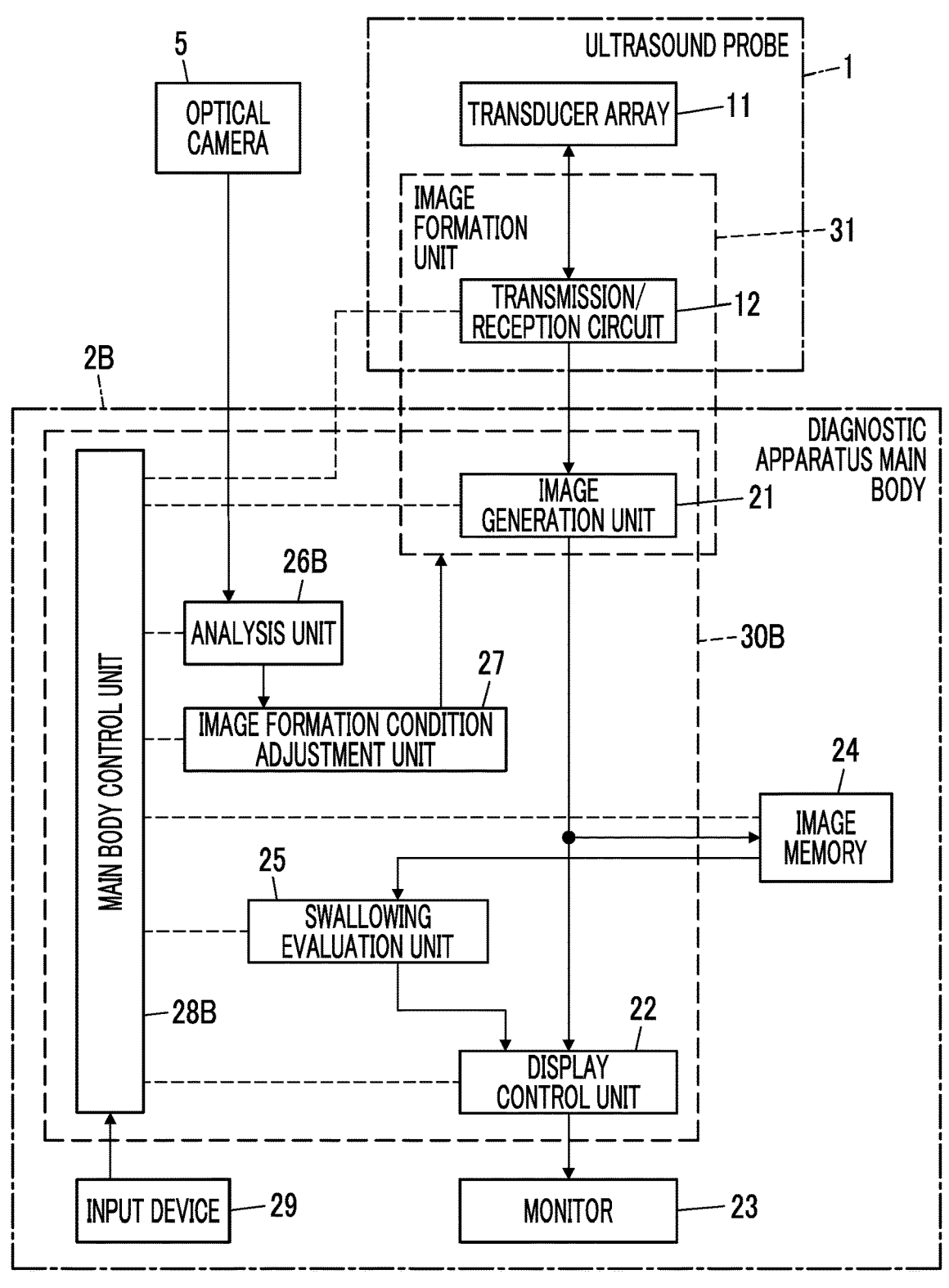
FIG. 7 is a block diagram showing a configuration of a diagnostic apparatus main body in Embodiment 3.

FIG. 7 shows a configuration of an ultrasound diagnostic apparatus according to Embodiment 3 of the present invention. The ultrasound diagnostic apparatus according to Embodiment 3 is an ultrasound diagnostic apparatus in which an optical camera 5 is used instead of the motion sensor 3, a diagnostic apparatus main body 2B is used instead of the diagnostic apparatus main body 2, and the ultrasound probe 1 is connected to the diagnostic apparatus main body 2B in the ultrasound diagnostic apparatus of Embodiment 1 shown in FIG. 1. The diagnostic apparatus main body 2B uses an analysis unit 26B and a main body control unit 28B instead of the analysis unit 26 and the main body control unit 28 in the diagnostic apparatus main body 2 in Embodiment 1, and the other configurations are the same as those of the diagnostic apparatus main body 2 of Embodiment 1.

The ultrasound diagnostic apparatus according to Embodiment 3 acquires the chewing information of the subject by using an optical image.

The optical camera 5 is used for acquiring an optical image (video image) of a region including at least one of the mouth, the jaw, or the pharyngeal part of the subject during ingesting. The optical image acquired by the optical camera 5 is sent to the analysis unit 26B of the diagnostic apparatus main body 2B.

The optical camera 5 may be independent of the ultrasound probe 1 and the diagnostic apparatus main body 2A. Further, in a case of a handheld type compact ultrasound diagnostic apparatus, the optical camera 5 may be incorporated in the diagnostic apparatus main body 2A. As long as it is possible to image a region including at least one of the mouth, the jaw, or the pharyngeal part of the subject, the optical camera 5 may be disposed in front of the face of the subject or at a position to capture the profile of the face of the subject. It is preferable to perform imaging at an angle where the face of the subject is viewed from below because it is easy to grasp the motions of the mouth, the jaw, and the pharyngeal part of the subject.

In addition, it is preferable that the optical camera 5 includes a wide-angle lens such that the subject can be easily put into the imaging range. A 360-degree camera can also be used as the optical camera 5.

The analysis unit 26B constitutes the chewing information acquisition unit together with the optical camera 5, and acquires the chewing information regarding the chewing of the subject by analyzing an optical image (video image) acquired by the optical camera 5.

The analysis unit 26B can acquire the number of chewing movements, the strength of chewing, the habit of chewing, and the area of chewing on the basis of the movement amount of the feature points set in the mouth angle, the jaw, and the like of the subject from the magnitude of the optical flow (image difference) by calculating the movement amount of the feature points.

In addition, as the optical camera 5, a so-called time of flight (ToF) camera in which distance information to the subject can be obtained by a direct ToF method or an indirect ToF method can also be used, and in this case, the analysis unit 26B can acquire the chewing information by analyzing the movement of the point group corresponding to a plurality of feature points of the subject and grasping the motion of the pharyngeal part.

The image generation unit 21, the display control unit 22, the image memory 24, the swallowing evaluation unit 25, the analysis unit 26B, and the image formation condition adjustment unit 27, and the transmission/reception circuit 12 of the ultrasound probe 1 are connected to the main body control unit 28B, and the input device 29 is connected to the main body control unit 28B.

In addition, a processor 30B is composed of the image generation unit 21, the display control unit 22, the swallowing evaluation unit 25, the analysis unit 26B, the image formation condition adjustment unit 27, and the main body control unit 28B.

In the ultrasound diagnostic apparatus according to Embodiment 3, the chewing information of the subject is acquired by the chewing information acquisition unit composed of the optical camera 5 and the analysis unit 26B, and the image formation condition in the image formation unit 31 is adjusted to the optimal condition for the subject by the image formation condition adjustment unit 27 on the basis of the acquired chewing information. Then, the ultrasound image of the pharyngeal part of the subject during the swallowing of the jelly food containing air bubbles is acquired in accordance with the adjusted image formation condition, and the swallowing of the subject is evaluated by the swallowing evaluation unit 25 through the analysis of the ultrasound image.

The evaluation result by the swallowing evaluation unit 25 is displayed on the monitor 23 via the display control unit 22 together with the ultrasound image used for detecting the swallowing residue. At this time, the optical image (video image) acquired by the optical camera 5 can also be displayed on the monitor 23 together with the ultrasound image and the evaluation result.

Even in a case in which the chewing information acquisition unit is composed of the optical camera 5 and the analysis unit 26B and the chewing information of the subject is acquired by using an optical image as in Embodiment 3, the ultrasound image can be acquired in accordance with the image formation condition adjusted to the optimal condition for the subject, and dysphagia can be accurately evaluated, as in Embodiments 1 and 2.

Embodiment 4

Figure 8:
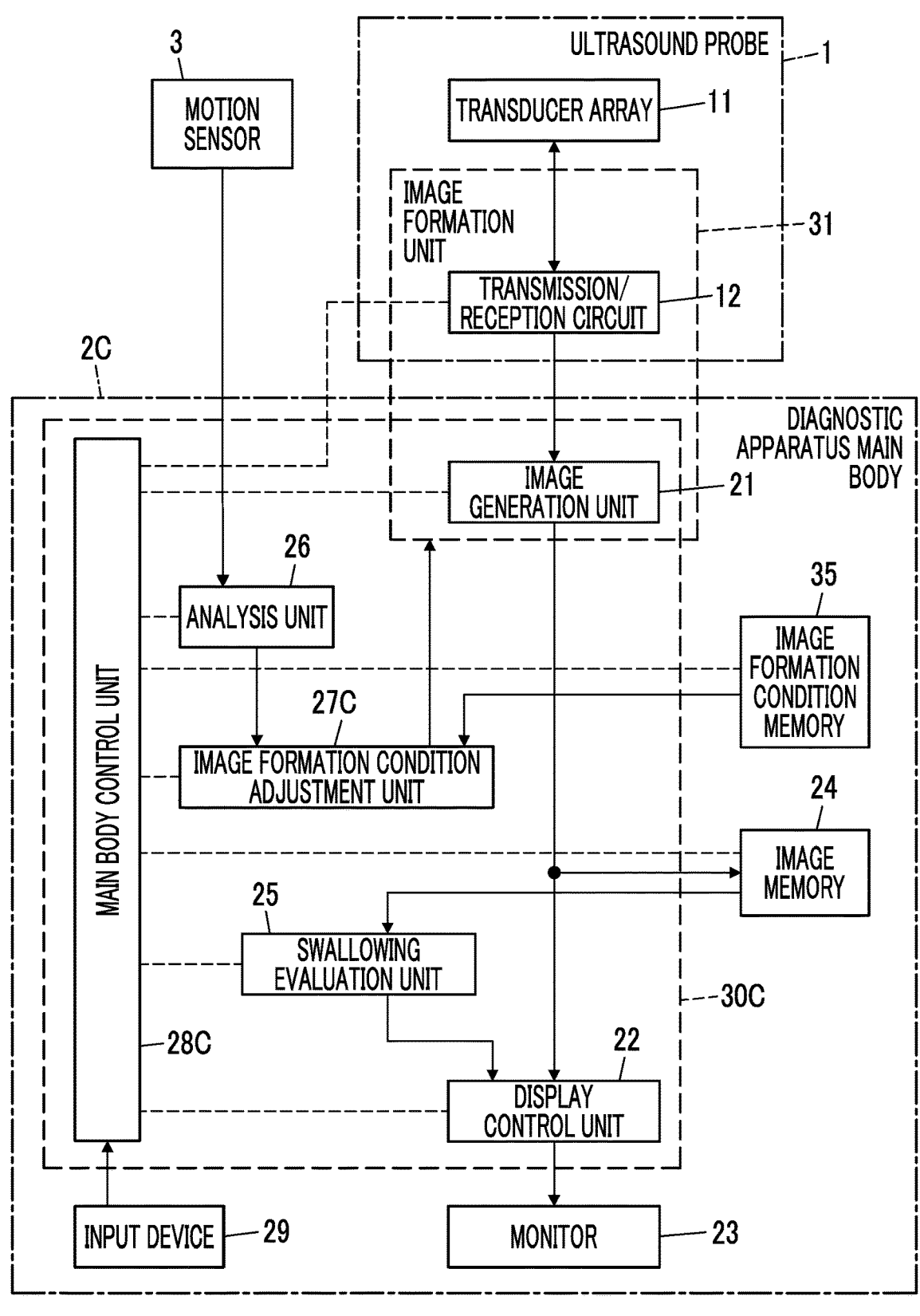
FIG. 8 is a block diagram showing a configuration of a diagnostic apparatus main body in Embodiment 4.

FIG. 8 shows a configuration of an ultrasound diagnostic apparatus according to Embodiment 4 of the present invention. The ultrasound diagnostic apparatus according to Embodiment 4 is an ultrasound diagnostic apparatus in which a diagnostic apparatus main body 2C is used instead of the diagnostic apparatus main body 2, and the ultrasound probe 1 and the motion sensor 3 are connected to the diagnostic apparatus main body 2C in the ultrasound diagnostic apparatus of Embodiment 1 shown in FIG. 1. The diagnostic apparatus main body 2C is a diagnostic apparatus main body in which an image formation condition memory 35 is newly provided and an image formation condition adjustment unit 27C and a main body control unit 28C are used instead of the image formation condition adjustment unit 27 and the main body control unit 28 in the diagnostic apparatus main body 2 in Embodiment 1, and the other configurations are the same as those of the diagnostic apparatus main body 2 of Embodiment 1. The image formation condition memory 35 is connected to the image formation condition adjustment unit 27C.

The ultrasound diagnostic apparatus according to Embodiment 4 uses an image formation condition preset for each subject as initial parameters.

The image formation condition preset for each subject is stored in the image formation condition memory 35, and for example, in a case in which the subject identifier (ID) for authenticating the subject is input from the input device 29, the image formation condition adjustment unit 27C reads out the image formation condition corresponding to the subject from the image formation condition memory 35 and adjusts the image formation condition with the read-out image formation condition as the initial parameters.

Examples of the image formation condition preset for each subject include the gain (brightness) and the harmonic imaging, which are related to the ease of passage of ultrasound waves caused by the composition of the subcutaneous tissue and the like, the depth and the focus position, which are related to the thickness of the neck and the amount of muscle, and the frame rate, which is related to the speed of chewing and swallowing.

As the image formation condition memory 35, recording media such as a flash memory, an HDD, an SSD, an FD, a MO disc, an MT, a RAM, a CD, a DVD, an SD card, or a USB memory, a server, or the like can be used.

The image generation unit 21, the display control unit 22, the image memory 24, the swallowing evaluation unit 25, the analysis unit 26, the image formation condition adjustment unit 27C, and the image formation condition memory 35, and the transmission/reception circuit 12 of the ultrasound probe 1 are connected to the main body control unit 28C, and the input device 29 is connected to the main body control unit 28C.

In addition, a processor 30C is composed of the image generation unit 21, the display control unit 22, the swallowing evaluation unit 25, the analysis unit 26, the image formation condition adjustment unit 27C, and the main body control unit 28C.

In a case of performing the evaluation examination for the swallowing of the subject, first, the subject ID is input from the input device 29, and the image formation condition corresponding to the subject is read out from the image formation condition memory 35 by the image formation condition adjustment unit 27C.

The image formation condition adjustment unit 27C sets the read-out image formation condition as the initial parameters, and the initial parameters are adjusted to the optimal parameters on the basis of the chewing information of the subject acquired by the chewing information acquisition unit composed of the motion sensor 3 and the analysis unit 26. Then, the ultrasound image of the pharyngeal part of the subject during the swallowing of the jelly food containing air bubbles is acquired in accordance with the adjusted image formation condition, and the swallowing is evaluated by the swallowing evaluation unit 25 on the basis of the ultrasound image.

In this way, by adjusting the preset image formation condition that corresponds to the subject to the optimal condition on the basis of the chewing information, it is possible to acquire an ultrasound image better suited for detecting the swallowing residue of the subject and to more accurately evaluate dysphagia.

Although the image formation condition adjustment unit 27C may adjust the image formation condition of the subject preset in the image formation condition memory 35 to the optimal condition for the subject by increasing parameters such as the gain, the contrast, and the frame rate on the basis of the chewing information, it is possible to adjust the image formation condition to the optimal condition by decreasing the parameters of the image formation condition depending on the preset image formation condition.

Further, a temporal change in the chewing information of the subject is acquired by the chewing information acquisition unit, and the image formation condition adjustment unit 27C can also adjust the parameters of the image formation condition in real time in accordance with the acquired change in the chewing information. For example, the range of increasing or decreasing the parameters such as the gain and the contrast can be adjusted in conformity with an increase or decrease in the number of chewing movements acquired by the chewing information acquisition unit. As a result, it is possible to always acquire an ultrasound image suitable for detecting the swallowing residue even in a case in which the chewing information fluctuates.

Further, instead of storing the image formation condition preset for each subject in the image formation condition memory 35, it is also possible to store the image formation condition preset for each category in the image formation condition memory 35 by categorizing the swallowing characteristics of the subject.

The categorization of the swallowing characteristics can be performed, for example, by pattern matching of the waveform pattern of the myoelectric potential detected by the myoelectric sensor as the motion sensor 3. Pattern matching may be performed by correlating the entire waveform for each subject, or pattern matching may be performed by converting the peak value, the frequency, and the like of the waveform into feature amounts and correlating the feature amounts.

Such categorization of the swallowing characteristics can be performed using a determination model that has been trained using a machine learning technique such as deep learning.

Embodiment 4 described above has been applied to the ultrasound diagnostic apparatus including the chewing information acquisition unit composed of the motion sensor 3 and the analysis unit 26 as in Embodiment 1. In the same manner, Embodiment 4 can also be applied to the ultrasound diagnostic apparatus including the chewing information acquisition unit composed of the microphone 4 and the analysis unit 26A as in Embodiment 2.

In a case in which the swallowing characteristics of the subject are categorized and the image formation condition is preset for each category, categorization may be performed by correlating the entire waveform for each subject with respect to the waveform patterns of the swallowing sound detected by the microphone 4 to perform pattern matching, or categorization may be performed by converting the peak value, the frequency, and the like of the waveform of the swallowing sound into feature amounts and correlating the feature amounts to perform pattern matching.

In a case of categorizing the swallowing characteristics using a determination model that has been trained using a machine learning technique such as deep learning, it is possible to train the determination model by recording and inputting the plurality of swallowing sound waveform patterns for each subject to a neural network.

Further, in the same manner, Embodiment 4 can also be applied to the ultrasound diagnostic apparatus including the chewing information acquisition unit composed of the optical camera 5 and the analysis unit 26B as in Embodiment 3.

The connection method between the ultrasound probe 1 and the diagnostic apparatus main bodies 2, 2A, 2B, and 2C in Embodiments 1 to 4 is not particularly limited and may be a wired connection or a wireless connection. In addition, the connection method between the motion sensor 3 and the diagnostic apparatus main bodies 2 and 2C in Embodiments 1 and 4, the connection method between the microphone 4 and the diagnostic apparatus main body 2A in Embodiment 2, and the connection method between the optical camera 5 and the diagnostic apparatus main body 2B in Embodiment 3 are also not particularly limited and may be a wired connection or a wireless connection.

In Embodiments 1 to 4 described above, the ultrasound probe 1 includes the transmission/reception circuit 12, but a configuration can also be employed in which the diagnostic apparatus main bodies 2, 2A, 2B, and 2C include the transmission/reception circuit 12. In addition, although the diagnostic apparatus main bodies 2, 2A, 2B, and 2C include the image generation unit 21, the ultrasound probe 1 may include the image generation unit 21. Further, as shown in FIG. 4, a configuration may be employed in which, among the signal processing unit 32, the DSC 33, and the image processing unit 34 that constitute the image generation unit 21, the ultrasound probe 1 includes only the signal processing unit 32, and the diagnostic apparatus main body 2, 2A, 2B, and 2C include the DSC 33 and the image processing unit 34.

As the diagnostic apparatus main bodies 2, 2A, 2B, and 2C in Embodiments 1 to 4, a portable or handheld type diagnostic compact apparatus main body can also be used, or a stationary diagnostic apparatus main body can also be used.

EXPLANATION OF REFERENCES

1: ultrasound probe
2, 2A, 2B, 2C: diagnostic apparatus main body
3: motion sensor
3A: sensor main body
3B: adhesive seal
3C: cable
4: microphone
5: optical camera
11: transducer array
12: transmission/reception circuit
13: pulsar
14: amplification unit
15: AD conversion unit
16: beam former
21: image generation unit
22: display control unit
23: monitor
24: image memory
25: swallowing evaluation unit
26, 26A, 26B: analysis unit
27, 27A, 27B, 27C: image formation condition adjustment unit
28, 28A, 28B, 28C: main body control unit
29: input device
30, 30A, 30B, 30C: processor
31: image formation unit
32: signal processing unit
33: DSC
34: image processing unit
35: image formation condition memory

What is claimed is:

1. An ultrasound diagnostic apparatus comprising:
an ultrasound probe; and
a processor configured to:
    acquire chewing information during chewing of a subject;
    adjust a predetermined first image formation condition to a second image formation condition suitable for detecting a swallowing residue of the subject on the basis of the acquired chewing information;
    acquire an ultrasound image of a pharyngeal part of the subject in accordance with the second image formation condition by transmitting and receiving an ultrasound beam using the ultrasound probe; and
    evaluate whether or not the subject has dysphagia and a degree of dysphagia on the basis of the ultrasound image acquired,
wherein the processor acquires at least one of a number of chewing movements, a strength of chewing, a habit of chewing, or an area of chewing as the chewing information, and wherein the processor adjusts the first image formation condition to the second image formation condition to increase brightness, contrast, and resolution as the number of chewing movements, the strength of chewing, or the area of chewing acquired as the chewing information increases.

2. The ultrasound diagnostic apparatus according to claim 1,
wherein the processor acquires the ultrasound image of the pharyngeal part of the subject in a case in which a jelly food containing air bubbles is swallowed, in accordance with the second image formation condition.

3. The ultrasound diagnostic apparatus according to claim 1,
wherein the processor adjusts the first image formation condition to the second image formation condition to increase a frame rate as the number of chewing movements, the strength of chewing, or the area of chewing acquired as the chewing information increases.

4. The ultrasound diagnostic apparatus according to claim 3, comprising a motion sensor that is attached to the subject and that detects a motion of at least one of a mouth, a jaw, or the pharyngeal part of the subject,
wherein the processor acquires the chewing information by analyzing the motion detected by the motion sensor.

5. The ultrasound diagnostic apparatus according to claim 4,
wherein the motion sensor includes at least one of a myoelectric sensor, an acceleration sensor, or a vibration sensor.

6. The ultrasound diagnostic apparatus according to claim 3, comprising a microphone that acquires a chewing sound,
wherein the processor acquires the chewing information by analyzing the chewing sound acquired by the microphone.

7. The ultrasound diagnostic apparatus according to claim 3, comprising an optical camera that acquires an optical image of a region including at least one of a mouth, a jaw, or the pharyngeal part of the subject,
wherein the processor acquires the chewing information by analyzing the optical image acquired by the optical camera.

8. An ultrasound diagnostic apparatus comprising:
an ultrasound probe; and
a processor configured to:
    acquire chewing information during chewing of a subject;
    adjust a predetermined first image formation condition to a second image formation condition suitable for detecting a swallowing residue of the subject on the basis of the acquired chewing information;
    acquire an ultrasound image of a pharyngeal part of the subject in accordance with the second image formation condition by transmitting and receiving an ultrasound beam using the ultrasound probe; and
    evaluate whether or not the subject has dysphagia and a degree of dysphagia on the basis of the ultrasound image acquired,
wherein the processor acquires at least one of a number of chewing movements, a strength of chewing, a habit of chewing, or an area of chewing as the chewing information, and
wherein the processor adjusts the first image formation condition to the second image formation condition to increase a frame rate as the number of chewing movements, the strength of chewing, or the area of chewing acquired as the chewing information increases.

9. The ultrasound diagnostic apparatus according to claim 8,
wherein the processor acquires the ultrasound image of the pharyngeal part of the subject in a case in which a jelly food containing air bubbles is swallowed, in accordance with the second image formation condition.

10. An ultrasound diagnostic apparatus comprising:
an ultrasound probe;
a processor configured to:
    acquire chewing information during chewing of a subject;
    adjust a predetermined first image formation condition to a second image formation condition suitable for detecting a swallowing residue of the subject on the basis of the acquired chewing information;
    acquire an ultrasound image of a pharyngeal part of the subject in accordance with the second image formation condition by transmitting and receiving an ultrasound beam using the ultrasound probe; and
    evaluate whether or not the subject has dysphagia and a degree of dysphagia on the basis of the ultrasound image acquired; and
an optical camera that acquires a video image of a region including at least one of a mouth, a jaw, or the pharyngeal part of the subject,
wherein the processor acquires the chewing information by analyzing the video image acquired by the optical camera.

11. The ultrasound diagnostic apparatus according to claim 10,
wherein the processor acquires the ultrasound image of the pharyngeal part of the subject in a case in which a jelly food containing air bubbles is swallowed, in accordance with the second image formation condition.

12. An ultrasound diagnostic apparatus comprising:
an ultrasound probe; and
a processor configured to:
    acquire chewing information during chewing of a subject;
    adjust a predetermined first image formation condition to a second image formation condition suitable for detecting a swallowing residue of the subject on the basis of the acquired chewing information;
    acquire an ultrasound image of a pharyngeal part of the subject in accordance with the second image formation condition by transmitting and receiving an ultrasound beam using the ultrasound probe; and
    evaluate whether or not the subject has dysphagia and a degree of dysphagia on the basis of the ultrasound image acquired,
wherein the processor uses machine learning to adjust the first image formation condition to the second image formation condition on the basis of the chewing information.

13. The ultrasound diagnostic apparatus according to claim 12,
wherein the processor acquires the ultrasound image of the pharyngeal part of the subject in a case in which a jelly food containing air bubbles is swallowed, in accordance with the second image formation condition.

14. The ultrasound diagnostic apparatus according to claim 12,
wherein the processor acquires at least one of a number of chewing movements, a strength of chewing, a habit of chewing, or an area of chewing as the chewing information, wherein the processor adjusts the first image formation condition to the second image formation condition to increase brightness, contrast, and resolution, and to increase a frame rate as the number of chewing movements, the strength of chewing, or the area of chewing acquired as the chewing information increases.

15. The ultrasound diagnostic apparatus according to claim 12, comprising a motion sensor that is attached to the subject and that detects a motion of at least one of a mouth, a jaw, or the pharyngeal part of the subject, wherein the processor acquires the chewing information by analyzing the motion detected by the motion sensor.

16. The ultrasound diagnostic apparatus according to claim 15, wherein the motion sensor includes at least one of a myoelectric sensor, an acceleration sensor, or a vibration sensor.

17. The ultrasound diagnostic apparatus according to claim 12, comprising a microphone that acquires a chewing sound, wherein the processor acquires the chewing information by analyzing the chewing sound acquired by the microphone.

18. The ultrasound diagnostic apparatus according to claim 12, comprising an optical camera that acquires an optical image of a region including at least one of a mouth, a jaw, or the pharyngeal part of the subject, wherein the processor acquires the chewing information by analyzing the optical image acquired by the optical camera.

19. The ultrasound diagnostic apparatus according to claim 12, comprising an optical camera that acquires a video image of a region including at least one of a mouth, a jaw, or the pharyngeal part of the subject, wherein the processor acquires the chewing information by analyzing the video image acquired by the optical camera.

20. The ultrasound diagnostic apparatus according to claim 12, wherein the processor has an initial parameter of the first image formation condition set for each subject.

\* \* \* \* \*